United States Patent
Fargahi

(10) Patent No.: US 9,604,032 B2
(45) Date of Patent: Mar. 28, 2017

(54) ELASTIC CAP FOR THE PROTECTION OF THE DISTAL END OF A CATHETER HAVING AN INNER AND AN OUTER HOSE

(75) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 227 days.

(21) Appl. No.: 13/457,241

(22) Filed: Apr. 26, 2012

(65) Prior Publication Data

US 2012/0290064 A1   Nov. 15, 2012

Related U.S. Application Data

(60) Provisional application No. 61/484,247, filed on May 10, 2011.

(51) Int. Cl.
*A61M 25/00* (2006.01)
*A61F 2/95* (2013.01)

(52) U.S. Cl.
CPC .......... *A61M 25/0069* (2013.01); *A61F 2/95* (2013.01); *A61M 2025/0004* (2013.01)

(58) Field of Classification Search
CPC .......... A61M 25/0069; A61M 25/0074; A61M 2025/0004; A61M 2025/0006; A61M 2025/0014; A61M 2025/0079; A61M 3/0279; A61M 25/001; A61M 25/0067; A61M 25/008; A61F 2/95
USPC ...... 606/108, 190–200; 623/1.11–1.12, 1.23; 604/523, 533–535, 263, 264
See application file for complete search history.

(56) References Cited

U.S. PATENT DOCUMENTS

| | | | |
|---|---|---|---|
| 8,585,680 B2 * | 11/2013 | Magnuson et al. ........... | 604/529 |
| 2001/0000350 A1 * | 4/2001 | Durcan et al. ............... | 623/1.11 |
| 2002/0049451 A1 * | 4/2002 | Parmer et al. ................ | 606/108 |
| 2002/0165554 A1 * | 11/2002 | Dworschak et al. ......... | 606/108 |
| 2002/0198440 A1 * | 12/2002 | Snow ............................ | 600/116 |
| 2003/0032920 A1 * | 2/2003 | Wantink ........................ | 604/103 |
| 2005/0021046 A1 * | 1/2005 | Bilge ............................ | 606/108 |
| 2005/0115624 A1 * | 6/2005 | Walak ........................... | 138/139 |
| 2005/0187536 A1 * | 8/2005 | Shelso et al. ................ | 604/528 |
| 2005/0251102 A1 * | 11/2005 | Hegland et al. ............. | 604/500 |
| 2006/0142697 A1 * | 6/2006 | Hawk et al. ................. | 604/117 |
| 2006/0142702 A1 * | 6/2006 | Sievers et al. ............... | 604/264 |
| 2006/0173422 A1 * | 8/2006 | Reydel et al. ................ | 604/271 |
| 2006/0200188 A1 * | 9/2006 | Nance et al. ................. | 606/198 |
| 2006/0259120 A1 | 11/2006 | Vongphakdy et al. | |
| 2007/0219466 A1 * | 9/2007 | Tremulis et al. ............ | 600/585 |
| 2007/0282367 A1 * | 12/2007 | Jeffrey et al. ................ | 606/194 |

(Continued)

FOREIGN PATENT DOCUMENTS

FR    2707505 A1    1/1995

Primary Examiner — David C Eastwood
(74) Attorney, Agent, or Firm — Wagenknecht IP Law Group PC

(57) ABSTRACT

An elastic cap for covering the distal end of a catheter having inner and outer hoses, characterized in that the cap consists essentially of an elastic material, has a cavity in which the distal end of the inner and the outer hose of a catheter can be received, and the cap has a first opening via which the cavity is accessible from the outside, wherein prior to receiving the distal end of the catheter, the first opening has a diameter which is not larger than the outer diameter of the inner hose of the catheter and wherein the first opening is elastically expandable to a diameter which corresponds to the outer diameter of the outer hose.

15 Claims, 3 Drawing Sheets

(56) References Cited

U.S. PATENT DOCUMENTS

2008/0193211 A1* 8/2008 Burton et al. ............... 403/332
2010/0069852 A1    3/2010 Kelley
2010/0160863 A1    6/2010 Heuser
2012/0095432 A1* 4/2012 Nath ............................ 604/500

* cited by examiner

ELASTIC CAP FOR THE PROTECTION OF THE DISTAL END OF A CATHETER HAVING AN INNER AND AN OUTER HOSE

CROSS REFERENCE TO RELATED APPLICATIONS

This invention claims benefit of priority to U.S. patent application Ser. No. 61/484,247, filed May 10, 2011; the entire contents of which are herein incorporated by reference in their entirety.

TECHNICAL FIELD

The invention relates to an elastic cap for a catheter and to a catheter having an elastic cap.

BACKGROUND

The implantation of stents has established itself as one of the most effective measures for the treatment of vascular diseases. Stents have the purpose to take on a support function in the hollow organs of a patient. One of the main application areas of such stents is to permanently or temporarily widen and keep open vascoconstrictions, in particular constrictions (stenoses) of the coronary vessels. Apart from that, for example, aneurysm stents are known which serve for supporting damaged vascular walls. Stents of conventional design have a tubular base body with a filigree support structure of metallic struts, wherein said base body, for insertion into the body, is initially present in a compressed form and expands at the site of application. For placing stents, usually, catheters having an inner hose and an outer hose are used as an application device. It is possible here to use different catheters having inner and outer hoses.

For the application of self-expandable stents, balloon catheters are most commonly used. For this, the stent is mostly fixed by means of so-called "crimping" on a surface of the non-dilated balloon situated on the inner hose of the catheter and is protected against damage during the positioning of the catheter by overlapping with an outer hose. After the balloon catheter carrying the stent has been inserted into the vessel and the stent has reached the site of the intended application, the outer hose is drawn back and the balloon dilates. Thereby, the stent is expanded and to contact the vascular wall. Once the stent has been sufficiently widened and the vessel has been sufficiently expanded, the pressure in the balloon is reduced, the balloon returns to a non-dilated state and the catheter can be removed again, whereas the applied stent remains in the vessel and keeps the same open. Suitable balloon catheters for stent application are well known and are described exemplary in DE 102 15 462.

Alternatively, a self-expandable stent design can be used. Application devices for applying self-expandable stents usually do not have a dilatable balloon for stent application. Here, mostly catheter devices are used which have an inner hose and an outer hose, wherein the stent to be applied is initially fixed or crimped onto a surface of the inner hose and covered by an outer hose slid thereon. In the crimped form, self-expandable stents have a radial force which presses the outer surface of the stent against the outer hose's inner surface covering the stent. The catheter is introduced into the vessel until the stent reaches the site where the stent is to be applied. For application, the outer hose is now drawn back until the entire stent is exposed. Due to the radial force, the stent expands automatically, becomes detached from the inner hose and contacts the vascular wall. Once the stent has sufficiently dilated, the catheter can be removed again whereas the applied stent remains in the vessel and keeps the same open. Suitable catheters for the application of self-expandable stents are well known and are described exemplary in U.S. Pat. No. 5,824,041.

One problem of these catheters having an inner and an outer hose is that during positioning the catheter in the vascular system of the patient, uncontrolled and sometimes high loads act on the distal end of the inner and outer hoses. This can in particular result in that the hose wall at the distal end of the outer hose is irreversibly stretched and a so-called "fish mouth" is formed. Said "fish mouth" formation can contribute to injuries of the vascular wall during the application of the catheter as well as during the removal of the catheter and can result in malfunctions during catheter positioning.

SUMMARY

It is the object of the present invention to reduce or avoid one or more disadvantages of the prior art. It is in particular an object of the present invention to provide means which allow an improved protection of the distal end of a catheter having an inner and an outer hose.

The present invention solves this object by providing an elastic cap for covering the distal end of a catheter having inner and outer hoses. The elastic cap is characterized in that the cap consists essentially of an elastic material, has a cavity in which the distal end of the inner and the outer hose of a catheter can be received, and the cap has a first opening via which the cavity is accessible from the outside, wherein prior to receiving the distal end of the inner hose, the first opening has a diameter which is not larger, preferably is smaller, than the outer diameter of the inner hose of the catheter and wherein the first opening is elastically expandable to a diameter which corresponds to the outer diameter of the outer hose of the catheter.

When applying the elastic cap onto the distal end of a catheter, the inner hose as well as the outer hose is covered in the region of the distal end by the cap. The distal end of the inner and the outer hose of the catheter are inserted through the first opening into the cavity of the elastic cap. The first opening is arranged at that end of the cap according to the invention which is located opposite to the insertion direction used during the catheter application. When attaching the cap according to the invention, the first opening is elastically expanded to be at least wide enough that in a region comprising the edge of the first opening, the inner surface of the cavity comes in contact with the outer surface of the outer hose and the cap thus overlaps with the outer hose. The catheter can now be applied without any risk.

Once the distal end of the catheter has reached the destination in the patient, the outer hose is drawn back and the distal end of the outer hose exits the cavity of the cap. As soon as the distal end of the outer hose has passed the first opening and thus is removed from the cap according to the invention, the diameter of the first opening contracts due to the elastic properties of the cap according to the invention and the cap rests in a region comprising the edge of the first opening against the outer surface of the inner hose. Thus, in the region of the first opening, a stepless transition from the inner hose to the elastic cap is created. Now, after the catheter has fulfilled its purpose, the same can be removed again without imposing excessive stress on the surrounding healthy tissue.

The use of the elastic cap according to the invention during the application of a catheter having an inner and an outer hose ensures that during the application of the catheter, the surfaces at the distal end of the inner and outer hoses of the catheter are protected against direct contact with the environment. The distal end of the outer hose is not deformed and no so-called "fish mouth" is formed. Thus, the stress for the patient during the application of the catheter is reduced and the risk of unintended impairment of healthy tissue is minimized. Therefore, the overall stress acting on the distal end of the catheter during the application decreases as well. As a result, the problems during a catheter application decrease such as, for example, a possible displacement of the outer hose across the distal end of the inner hose or damage or position changes of a stent which is to be placed with the catheter. The use of the cap according to the invention ensures also that the catheter can be removed again after the intended use without any risk because after the removal of the outer hose, due to the elastic properties of the cap material, the cap rests directly against the inner hose and therefore prevents the formation of potentially disturbing obstacles such as e.g. steps or burrs which could cause injuries when pulling out the catheter.

The cap according to the invention has an outer basic shape which, after attaching the cap on the distal end of a catheter, allows the insertion and movement of the catheter in the vascular bed of a patient without excessively stressing the surrounding tissue. For this purpose, the cap can have a basic shape which is elongated along the longitudinal axis, thus an elongated basic shape. The basic shape can be radially symmetrical. The elastic cap according to the invention can be characterized in that the cap's end opposing the first opening is formed as blunt tip. At the inventive cap's end opposing the first opening, a second opening can be provided which can be configured in such a manner that a guide wire for a catheter can be guided therethrough. The outer surface of the cap can be formed smooth or structured. The outer surface of the cap can be coated with one or a plurality of layers of one or a plurality of materials. The coating, for example, can serve for protecting the cap; the coating can also have radiopaque materials, e.g. for visualizing the cap in the body of a patient, or the coating can configured so as to prevent interactions of the cap surface with the environment prior to or during the application of a catheter equipped with the cap.

The cap according to the invention is made of an elastic material. Preferably, the cap is made of a substantially biocompatible and/or bioinert material. In particular, the cap according to the invention can be an elastic material which comprises or consists of silicones, polyamides (PA), copolyamides, polyether block amides (e.g. such with the brand name PEBAX), polyurethanes (PUR) and/or a mixture thereof. In order to allow the visibility of the cap during the application of a catheter equipped therewith, for example, a radiopaque material can be admixed to the elastic material of the cap according to the invention.

The cap according to the invention can be manufactured by conventional methods, e.g. by extrusion methods, spraying methods, casting methods and/or injection molding methods. Suitable methods are known to the person skilled in the art.

It is obvious for the person skilled in the art that the cap according to the invention has to be adapted in terms of its dimensions to the catheter type used therewith. The specification of absolute dimension is not very useful for the definition of the cap. The person skilled in the art understands that the dimensions of the cap can be reasonably defined only with regard to a catheter potentially to be used therewith, without the need that the respective catheter has to be integral part of the claims. Based on a particular catheter and the information provided in this description, the person skilled in the art is able without undue difficulty to produce a cap according to the invention which has the mentioned properties.

The cap according to the invention has a cavity which is formed in such a manner that the distal end of the inner hose of a catheter as well as the distal end of the outer hose of the catheter can be received therein. Here, the distal end of the inner and outer hoses is to be understood in each case as the free end of the hose part which is inserted into the body of the patient during the application of the catheter. The distal end comprises at least the immediate edge region around the free hose end including the frontal outer surface and at least a portion of the adjacent lateral outer surface of the respective hose part.

The cavity of the cap according to the invention can have a plurality of different regions. For example, the cavity can comprise a first region which serves for receiving the distal end of the inner hose and is configured in such a manner that in this region, the inner surface of the cavity can be brought in contact with the outer surface at the distal end of the inner hose. Said first region can be formed in such a manner that this region is suitable to receive the distal end of the inner hose whereas the distal end of the outer hose can not be received in this first region. This can be achieved, for example, in that the diameter in the first region of the cavity is selected such that said diameter is smaller than the outer diameter of the outer hose and, at the same time, is larger than or equal to the outer diameter of the inner hose. In a particular embodiment, the diameter in the first region of the cavity corresponds substantially to the outer diameter of the inner hose.

The cavity of the cap according to the invention can have a second region which is arranged between the first opening of the cap and the first region of the cavity. This second region serves for receiving the distal end of the outer hose and is configured for this purpose in such a manner that in this region, the inner surface of the cavity can be brought in contact with the outer surface of the distal end of the outer hose. This second region can be formed such that this region is suitable to preferably receive the distal end of the outer hose. This can be achieved, for example, in that the diameter in the second region of the cavity is selected in such a manner that said diameter is larger than the outer diameter of the inner hose and, at the same time, is larger than or equal to the outer diameter of the outer hose. In a particular embodiment, the diameter in the second region of the cavity corresponds substantially to the outer diameter of the outer hose.

In a preferred embodiment of the cap according to the invention, the diameter in the first region of the cavity is smaller than the outer diameter of the outer hose and the diameter in the second region of the cavity is larger than in the first region, particularly preferred corresponds the diameter in the first region of the cavity substantially to the outer diameter of the outer hose.

In the cap according to the invention, the cavity is accessible from the outside via a first opening and the distal end of a catheter having inner and outer hoses can be inserted via said opening into the cavity of the cap. The first opening is provided at that end of the cap which is opposite to the desired insertion direction during the application of the catheter. In a preferred embodiment, the cap according to the invention has a blunt tip and the first opening is provided at that end of the cap which is opposite to the blunt tip.

The first opening serves for receiving the distal end of the inner and outer hoses of a catheter in the cavity of the cap. For this, the first opening is configured in such a manner that prior to receiving the distal end of the catheter having an inner hose and an outer hose, said opening has a diameter which is not larger than the outer diameter of the inner hose of the catheter. Preferably, the diameter of the first opening prior to receiving the inner hose is smaller than the outer diameter of the inner hose. This ensures that in the region of the first opening, the edge region of the cap can rest tightly on the whole circumference of the outer surface of the inner hose. Due to the properties of the elastic material of the cap according to the invention, the first opening is elastically dilatable to a diameter which corresponds substantially to the outer diameter of the outer hose. This ensures that in the region of the first opening, the edge region of the cap can rest tightly on the whole circumference of the outer surface of the outer hose. Thus, the first opening of the cap according to the invention is formed to be elastic in such a manner that the edge region of the first opening can rest tightly on the outer surface of the outer hose as well as on the outer surface of the inner hose. This results in that when attaching the cap on the distal end of a catheter, the inner hose as well as the outer hose surrounding the latter can be inserted into the cavity of the cap. Now, the edge region of the first opening rests tightly against the outer surface of the outer hose and the catheter can be applied as intended, wherein the cap according to the invention protects the distal end of the catheter. As soon as the catheter has reached the desired position in the patient, the outer hose can be drawn back; the outer hose exits the cavity and leaves the cap while the inner house remains protected by the cap. After the removal of the outer hose and due to the elastic properties of the cap material, the edge region of the first opening closes tightly around the outer surface of the inner hose. This ensures that after removing the outer hose, no steps or burrs form between the cap and the inner hose and the catheter can thus be removed from the patient without any problems.

The cap can be configured in particular in such a manner that the elastic material is still in the linear-elastic range when the first opening is expanded to a diameter which corresponds to the outer diameter of the outer hose of the catheter.

In order to ensure that the edge region of the first opening of the cap according to the invention does not damage the outer hose and allows to withdraw the outer hose from the cap without requiring excessive force it is advantageous if the edge region exerts a force on the outer surface of the outer hose which force is not too high or too low. In particular, the elastic cap can be configured such that the opening can be expanded with a force of ≤2.5 MPa, preferred 0.5 MPa to 2.0 MPa, to a diameter which corresponds to the outer diameter of the outer hose of a catheter to be used with said cap. It is assumed here that the elastic material is in the elastic range and the force which has to be applied for the expansion corresponds substantially to the force with which the expanded region tries to return to its initial state.

In order to ensure that the edge region of the first opening of the cap according to the invention does not damage the inner hose and that after removal of the outer hose, a tight fitting of the edge region of the first opening on the outer surface of the inner hose is ensured it is advantageous if the edge region exerts a force on the outer surface of the inner hose which force is not too high or too low. In particular, the elastic cap can be configured such that the opening can be expanded with a force of ≤1.5 MPa, preferred 0.2 MPa to 0.5 MPa, to a diameter which corresponds to the outer diameter of the inner hose of a catheter to be used with said cap. It is assumed here that the elastic material is in the elastic range and the force which has to be applied for the expansion corresponds substantially to the force with which the expanded region tries to return to its initial state.

The present invention relates also to a catheter having an inner and an outer hose, characterized in that at its distal end, the catheter has an elastic cap according to the invention. In particular, the cap according to the invention can be attached on the catheter in such a manner that the second region of the cavity of the elastic cap contacts the outer surface of the side wall of the distal end of the outer hose. This ensures that the cap encloses the distal end of the catheter and overlaps with the outer hose.

In particular, the catheter can involve a catheter which is configured as application device for a stent. In addition to the elastic cap according to the invention, the catheter according to the invention can comprise a stent. The catheter according to the invention can be configured, for example, as device for applying self-expandable stents. Devices for applying self-expandable stents are characterized in that no means for active plastic deformation of a crimped stent are necessary such as, e.g., expanding balloons, which are usually provided on balloon catheters. Preferably, catheters are used which, instead of such a balloon, have an inner hose onto which the self-expandable stent can be fixed for the application. In addition, such a catheter has means which allow to prevent the fixed or crimped stent from self-expanding until the stent is brought to the predetermined position and then allow the initiation of the self-expansion of the stent. This can be achieved, for example, in that the self-expandable stent crimped onto the inner hose is surrounded by an outer hose in such a manner that the stent is prevented from self-expanding. Said outer hose can be formed in such a manner that it is possible to draw the outer hose back relative to the inner hose so that a region of the inner hose can be exposed on which the self-expandable stent is present in a crimped manner. Once the outer hose is drawn back far enough, the stent, due to its radial force, can disengage from the inner hose, expand automatically, and get in contact with the vascular wall.

DETAILED DESCRIPTION

The invention is explained in more detail hereinafter by means of exemplary embodiments.

Exemplary Embodiment 1

Figure 1:
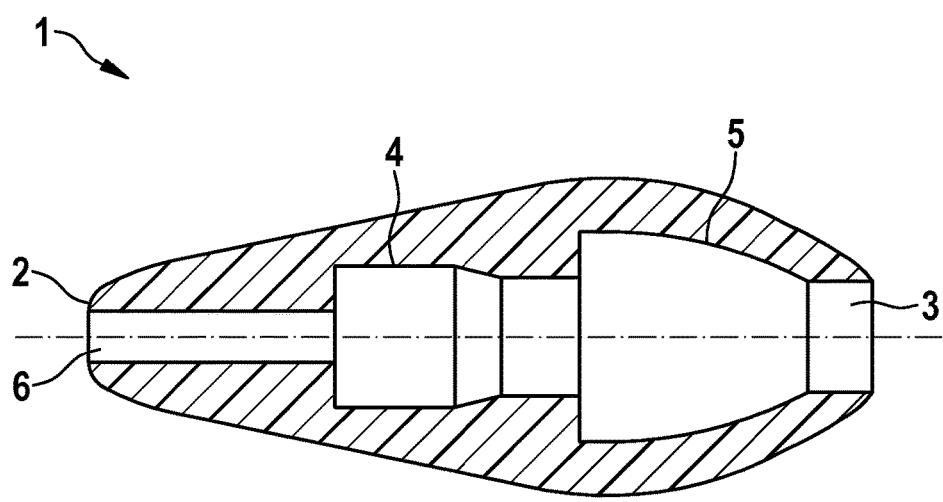
FIG. 1 shows a first embodiment of the cap according to the invention.

In FIG. 1, an embodiment of the elastic cap 1 according to the invention is illustrated.

The cap 1 is made from an elastic material and is manufactured as one piece in an injection molding process. The cap 1 has a radially symmetric, elongated basic shape and has a blunt tip 2 at a first end of the cap 1 and a first opening 3 at a second end of the cap, which second end is located opposite the first end. Inside the cap, there is a cavity which has a first region 4 and a second region 5. The first region 4 of the cavity is configured and dimensioned in such a manner that the distal end of the inner hose of a catheter can be received therein. If the cap is positioned on the distal end of a catheter having inner and outer hoses, the inner surface of the cavity in the first region 4 contacts the outer surface of the inner hose. The second region 5 of the cavity is configured and dimensioned in such a manner that the distal end of the outer hose of a catheter can be received therein. If the cap 1 is positioned on the distal end of the catheter, the inner surface of the cavity in the second region 5 contacts the outer surface of the outer hose.

The first opening 3 is configured in such a manner that the cavity is accessible from the outside via said opening. Prior to receiving the distal end of a catheter, the opening 3 has a diameter which is not larger than the outer diameter of the inner hose of the catheter. The first opening 3 is configured to be elastically expandable in such a manner that the opening 3 can be expanded to a diameter which corresponds to the outer diameter of the outer hose of the catheter.

Opposite to the first opening 3, the cap 1 has a second opening 6 through which the guide wire of a catheter can be inserted so that the catheter, after the cap 1 is attached to the distal end of the catheter, is still controllable via its guide wire.

Figure 2:
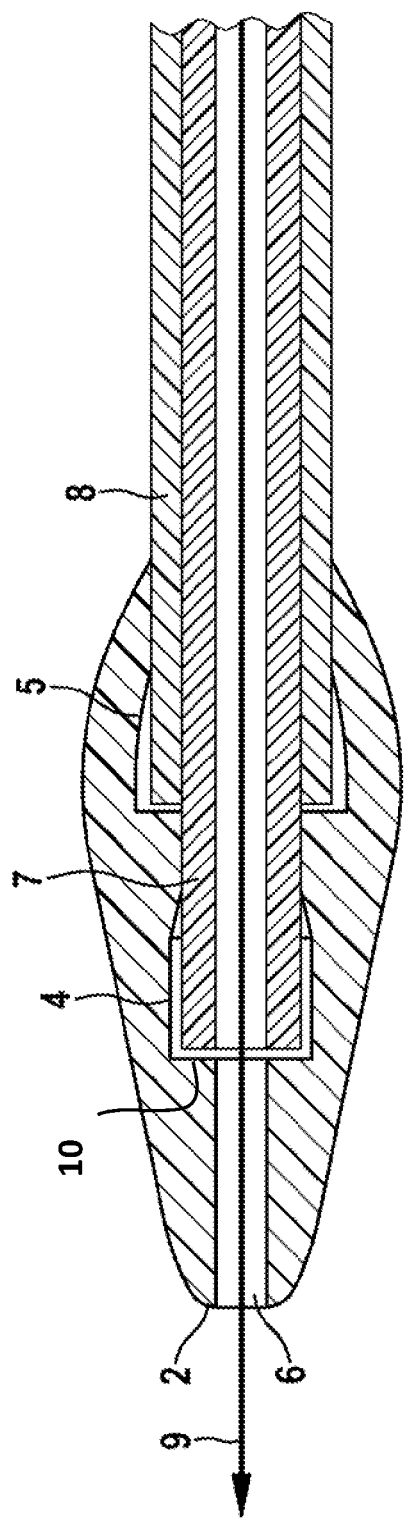
FIG. 2 shows a catheter having a cap according to the invention, wherein the cap overlaps with the outer hose.

In FIG. 2, a catheter is shown which has a cap 1 according to the invention as shown in FIG. 1. The cap 1 covers the distal end of the catheter, wherein the cap 1 overlaps with the inner hose 7 as well as with the outer hose 8 of the catheter. The guide wire 9 is guided across the inner wall 10 and through the second opening 6 and can be used for controlling the catheter during the application in the patient. The distal end of the inner hose 7 comes to lie proximate to the inner wall 10 in the first region 4 of the cavity of the cap 1 while the distal end of the outer hose 8 is positioned in the second region 5 of the cavity of the cap 1. The inner hose 7 as well as the outer hose 8 project through the first opening 3 into the cavity of the cap 1. In the region of the first opening 3, the edge region of the cap 1 rests tightly on the whole circumference of the outer surface of the outer hose. The distal end of the catheter is completely protected by the cap 1 and the catheter can be applied without any problems.

Figure 3:
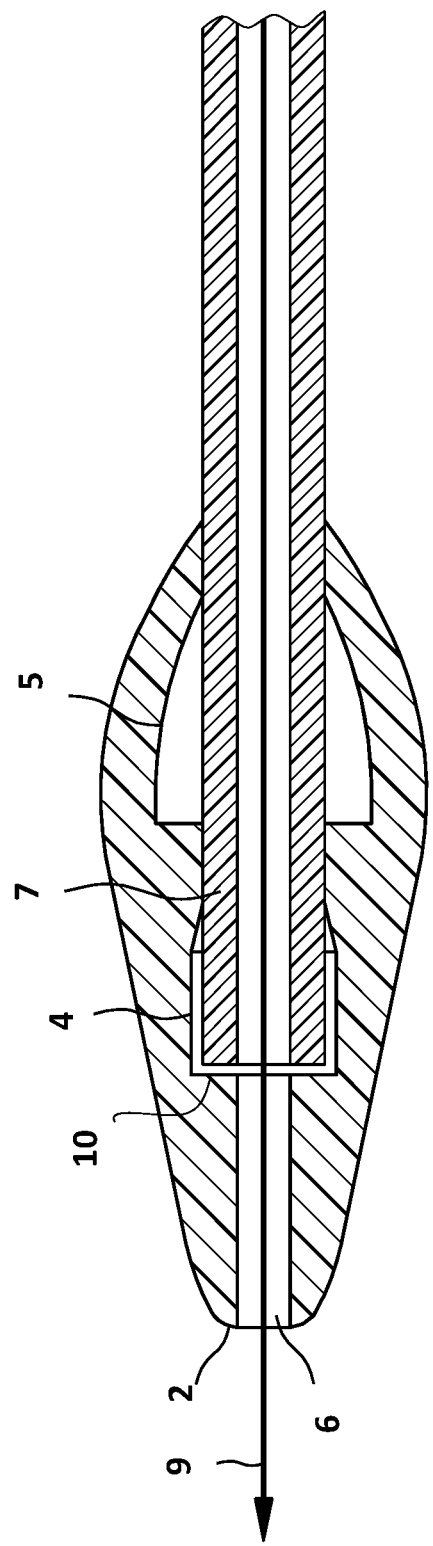
FIG. 3 shows a catheter having a cap according to the invention without an outer hose.

FIG. 3 illustrates the catheter of FIG. 2, wherein the outer hose 8 has been removed. After the outer hose has been drawn back and removed from the distal end region of the catheter, the distal end of the outer hose has left the cap 1 and the edge region of the cap 1 in the region of the first opening 3, due to the elastic properties of the cap material, has adapted itself in a tight manner to the whole circumference of the outer surface of the inner hose 7. The distal end of the catheter remains completely protected by the cap 1 and the catheter can be removed without any problems.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A catheter comprising an outer hose, an inner hose and an elastic cap for protectively covering the distal end of the catheter while inserted in a patient's vasculature, characterized in that the cap consists essentially of an elastic material, and comprises: a cavity comprising a first region with a diameter configured to accept and cover the distal end of the inner hose of the catheter and to exclude the distal end of the outer hose, and a second region with a diameter sized larger than the first region configured to releasably accept and cover the distal end of the outer hose of the catheter, and a first opening proximate to and accessing the second region of the cavity from outside of the cap, characterized in that the first opening is reversibly expandable under a force of less than or equal to 2.5 MPa between a diameter that is not larger than the diameter of the first region to a larger diameter that accepts the outer hose into the second region of the cavity thereby configuring the cap to close the first opening against the outer hose when the outer hose is covered by the cap and close the first opening against the inner hose when the outer hose is not covered by the cap so as to remain against the outer surface of the inner hose when withdrawing the catheter from the patient's vasculature.

2. The catheter according to claim 1, characterized in that the cap has an elongated basic shape along a longitudinal axis defined by the cavity.

3. The catheter according to claim 1, characterized in that the basic shape of the cap is radially symmetric along a longitudinal axis defined by the cavity.

4. The catheter according to claim 1, further comprising a blunt tip located at an end opposite to the first opening.

5. The catheter according to claim 1, characterized in that on a side opposite to the first opening, the cap has a second opening, wherein said second opening is configured in such a manner that a guide wire of the catheter can be guided therethrough.

6. The catheter according to claim 1, characterized in that the elastic material comprises or consists of a material selected from the group consisting of a silicone, a polyamide (PA), a copolyamide, a polyether block amide, a polyurethane (PUR), and a mixture thereof.

7. The catheter according to claim 1, characterized in that the cap is configured in such a manner during the expansion from the first diameter the elastic material is in a linear-elastic range.

8. The catheter according to claim 1, characterized in that the force is less than or equal to 1.5 MPa.

9. A catheter having an outer hose slidably disposed over an inner hose, characterized in that at its distal end, the catheter has an elastic cap for maintaining a protective cover over the distal end while the catheter is within a patient, wherein:
   the distal end of the inner hose is held and covered by a first region of a cavity within the cap and a distal end of the outer hose is held within a second region of the cavity within the cap that is proximate to the first region, further wherein the outer hose is held by an elastic edge proximate to the first opening, further wherein the elastic edge is configured to close against the inner hose after slidably removing the outer hose from the cap so as to remain against the outer surface of the inner hose when withdrawing the catheter from a patient's vasculature.

10. The catheter according to claim 9, characterized in that on a side opposite to the first opening, the cap has a second opening, wherein the second opening is configured in such a manner that a guide wire of the catheter can be guided therethrough.

11. The catheter according to claim 9, characterized in that the elastic material comprises or consists of a material selected from the group consisting of a silicone, a polyamide (PA), a copolyamide, a polyether block amide, a polyurethane (FUR), and a mixture thereof.

12. The catheter according to claim 9, characterized in that the cap is configured in such a manner during the expansion from a diameter that closes around the inner hose to a diameter that closes around the outer hose the elastic material is in a linear-elastic range.

13. The catheter according to claim 9, characterized in that the cap is configured in such a manner that the opening can be expanded with a force of ≤2.5 MPa to the diameter that closes around the outer hose of the catheter.

14. The catheter according to claim 13, characterized in that the force is less than or equal to 1.5 MPa.

15. The catheter according to claim 9, wherein the distal end of the inner hose remains held and covered by the first region of the cavity when the elastic edge is closed against the inner hose.

\* \* \* \* \*